United States Patent
Hoff et al.

(10) Patent No.: US 6,929,949 B1
(45) Date of Patent: Aug. 16, 2005

(54) CORONA ION GENERATING METHOD AND APPARATUS FOR THE MANIPULATION OF MOLECULES AND BIOLOGICAL CELLS

(75) Inventors: Drew Hoff, Tampa, FL (US); Mark J. Jaroszeski, Tampa, FL (US); Richard Gilbert, Tampa, FL (US); Richard Heller, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/250,219

(22) Filed: Jun. 13, 2003

Related U.S. Application Data

(60) Provisional application No. 60/319,316, filed on Jun. 14, 2002.

(51) Int. Cl.[7] .............................................. C12N 15/87
(52) U.S. Cl. ....................... 435/450; 435/461; 435/470; 435/285.2
(58) Field of Search ................................ 435/450, 461, 435/470, 285.2

(56) References Cited

U.S. PATENT DOCUMENTS

| | | | | |
|---|---|---|---|---|
| 4,413,897 A | * | 11/1983 | Kohyama | .................... 399/128 |
| 4,656,356 A | * | 4/1987 | Yoda et al. | .................. 250/326 |
| 5,869,326 A | | 2/1999 | Hofmann | |
| 5,983,131 A | | 11/1999 | Weaver et al. | |

* cited by examiner

*Primary Examiner*—James Ketter
(74) *Attorney, Agent, or Firm*—Molly L. Sauter; Smith & Hopen, P.A.

(57) ABSTRACT

The present invention provides a method and apparatus adapted to facilitate the entry of a preselected molecule into the intracellular space of a cellular sample through the use of ions generated by a corona charge source. With the present method and apparatus, molecules are manipulated within cells and in the extracellular space surrounding the cells. Manipulation enhances the permeability of cell barriers to allow the subsequent introduction of molecules of interest into the interior of a cell.

29 Claims, 15 Drawing Sheets

Basic Principle of Corona Charge Generation

CORONA ION GENERATING METHOD AND APPARATUS FOR THE MANIPULATION OF MOLECULES AND BIOLOGICAL CELLS

CROSS REFERENCE TO RELATED APPLICATION

This disclosure claims priority to U.S. provisional patent application No. 60/319,316, "Noncontact Corona Ion Generating Devices and Method for Manipulating Molecules and Biological Cells", by the same inventors, filed Jun. 14, 2002.

BACKGROUND OF INVENTION

Corona charges are ions that are generated in the atmosphere surrounding exposed electrical conductors. FIG. 1 illustrates the basic principles of corona charge generation. As known in the art, ions 1 are generated from the conductor 2 that is exposed to the local environment and held at a positive potential relative to the nearby conductor 3 that is at ground potential or floating. A power supply is typically used to apply the appropriate potentials to the conductors. The resulting ions are the driving force for moving molecules, modifying cells, and fusing cells. It is possible to apply a positive or a negative potential to one of the conductors to generate either positive or negative ions. Corona generating elements have been used for many years in devices that are familiar to most people. For example, photocopiers and laser printers use corona generators to impart a charge onto drums/rollers as part of the printing process. In addition, corona generators have been used in the materials handling industry to counter the charges that accumulate in rolled textiles and plastic films. Electrostatic precipitators use corona charge. In addition, the microelectronics industry uses corona charge for various applications.

It is known in the art to manipulate molecules and biological cells through the use of electroporation and electropermeabilization. Electroporation involves the application of a DC electric field to a cell whereby the electric field causes the induction of cell membrane breakdown. When a cell is in an electroporated state it is possible for molecules that do not normally penetrate the cell membrane to gain access to the cytosol. This effect has been exploited in vitro and in vivo for the delivery of drugs, DNA, and other therapeutic agents that have intracellular sites of action. Electroporation requires that physical contact be established between the target cells to be manipulated and the electrodes of the electroporation device. Electroporation techniques that rely on electrode contact cause muscle stimulation and discomfort. The prior art methods are invasive. Invasive treatment translates to increased complications due to infection and sterility, increased complexity of treatment procedures and increased patient discomfort. A need exists in the art for an apparatus and method adapted for the manipulation of molecules and biological cells that reduces patient discomfort and eliminates the inherent complications associated with traditional invasive methods of electroporation. However, in view of the prior art considered as a whole at the time the present invention was made, it was not obvious to those of ordinary skill in the pertinent art how the identified needs could be fulfilled.

SUMMARY OF INVENTION

The present invention provides a method and apparatus adapted to manipulate molecules and biological cells that is noninvasive. As such, the present invention reduces patient discomfort and eliminates the complications associated with traditional invasive procedures. Corona charge is a type of ion generation that results in the vicinity of separate conductors that are at different electrical potentials. Through the use of corona charge, molecules and cells in biological environments are manipulated by charges transmitted through the local atmosphere. No physical contact between the conductors or the corona generating elements and the cells or tissue is required.

In a preferred embodiment of the present invention, a method is provided to facilitate the manipulation of molecules of a cellular sample. The method includes providing a cellular sample, providing a corona charge source, establishing a corona charge in proximity to the cellular sample, and effecting manipulation of the molecules of the cellular sample.

In an additional embodiment, effecting manipulation of the molecules of the cellular sample increases the permeability of the outer barrier of a cell, or two or more cells of interest.

In yet another embodiment, the cells of the cellular sample are forced contact, the contact being sufficient to induce fusion of two or more cells.

In an additional embodiment, a bias potential source is provided and a bias potential is applied to the cellular sample.

Another embodiment of the present invention includes the introduction of a preselected molecule into the extracellular space of the cellular sample.

In another preferred embodiment, the preselected molecule that is introduced within the extracellular space of the cellular sample is manipulated by the application of the corona charge emitter.

In an additional embodiment, effecting manipulation of the molecules of the cellular sample increases the permeability of the outer barrier of a cell sufficient to allow the manipulation of the preselected molecule into the interior of the cell, or the manipulation of an intracellular molecule into the extracellular space of the cellular sample.

An apparatus adapted to facilitate the method of the present invention is described. The apparatus includes a support member, and at least one corona charge emitting device extending away from and affixed to or defining the support member, the corona charge emitting device adapted to establish a corona charge in proximity to the cellular sample for the effective manipulation of the molecules of the cellular sample.

In an additional embodiment of the apparatus, a spacer circumferentially encompassing the corona charge emitting device is provided, the spacer is used to define the proximity of the corona charge emitting device relative to the cellular sample. The spacer can be substantially transparent to allow viewing of the cellular sample.

In an additional embodiment of the apparatus, a restrictor circumferentially encompassing the corona charge emitting device is provided, the restrictor defines a restricted area of the cellular sample which the corona charge is established. The restricted area can be defined as circular, rectangular, elliptical, trapezoidal, polygonal, thomboidal or any other predetermined geometric configuration as required by the application of the apparatus of the invention. The restrictor can be substantially transparent to allow viewing of the cellular sample.

In yet another embodiment of the apparatus, the restrictor is physical in contact with the cellular sample, creating a substantially air tight cavity. An atmospheric controller allow for atmospheric control of the air within the cavity.

In an additional embodiment, a portal exists in the support member. The portal allows for the introduction of a molecule of interested into the cellular sample. A hypodermic needle or a jet injection apparatus can be positioned within the portal to accommodate the introduction of the molecule. Other introduction devices known in the art are within the scope of the invention.

In another preferred embodiment, a reservoir containing absorbent or porous material that contains the molecule of interest is positioned between the corona charge emitter and the cellular sample to allow introduction of a molecule of interest into the cellular sample from the reservoir.

In yet another embodiment, a holding apparatus is provided to contain the cellular sample. The cellular sample may be a nonliving matrix or other medium containing cells. The corona charge emitting device is moved in a predetermined direction relative to the cellular sample through physical or mechanical means. The corona charge emitting device serves to separate or sort cells dependent upon their charge potential. Additionally, the corona charge emitting device may be stationary and the cellular sample may be moved relative to the device.

The invention accordingly comprises the features of construction, combination of elements, and arrangement of parts that will be exemplified in the description set forth hereinafter and the scope of the invention will be indicated in the claims.

Other aspects and advantages of the present invention can be seen upon review of the figures, the detailed description, and the claims, which follow.

DETAILED DESCRIPTION

Figure 1:
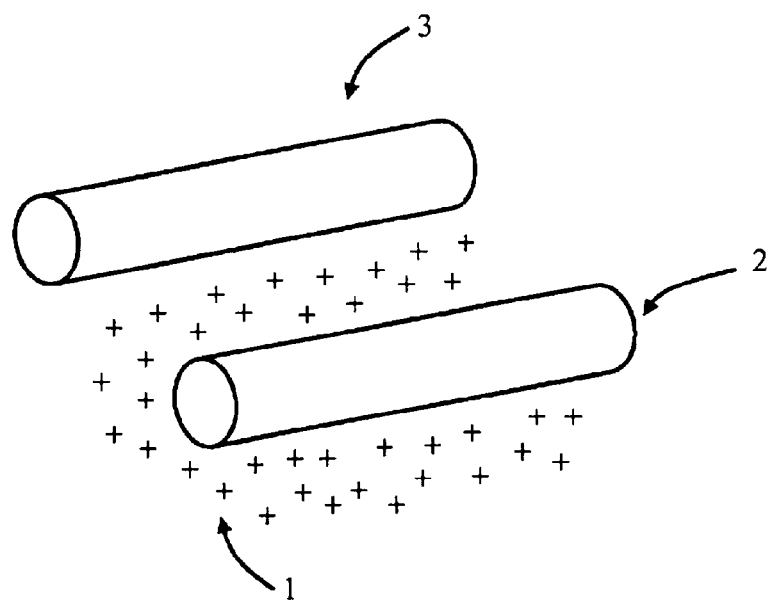
FIG. 1 illustrates the basic principle of corona charge generation known in the art.
Figure 2:
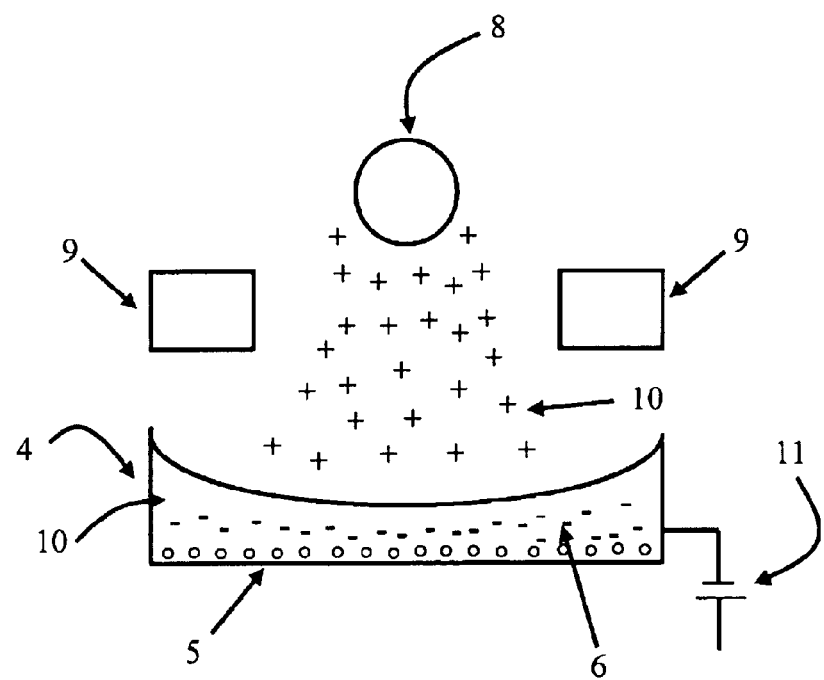
FIG. 2 illustrates the experimental apparatus used to facilitate the internalization of calcein by living biological cells in culture.

Referring initially to FIG. 2, the present invention has been used experimentally to facilitate the uptake of calcein by cells in culture. The experimental apparatus is shown as in FIG. 2. 35 mm diameter cell culture plates 4 were seeded with $0.5 \times 10^6$ human A204 sarcoma cells 5 approximately 24 hours prior to the experiment to allow time for the cells to attach to the growth surface on the bottom of each dish. Immediately prior to treating the cells with corona charge in air, the growth media was aspirated. Then 500 µl of 10 µM Calcein 6, in phosphate buffered saline 7; was introduced onto the bottom of the plate. Calcein molecules in the phosphate buffered saline are shown in the figure as a negatively charged species. The liquid was distributed over the entire growth surface. Then, the cells were exposed to a positive corona charge by placing them 2.5 cm away from a 5 inch long wire 8 set at a potential of 6000 V. FIG. 2 shows the cross-section of this wire along with the two ground conductors 9. Corona charge 10 was deposited onto the samples in the presence of calcein for a range of times from 0 minutes to 10 minutes. The solution of calcein was allowed to remain in contact with each sample for a period of 10 minutes after corona exposure. Additionally, a positive or negative bias potential 11 can be applied to the sample. Each plate was then washed with two separate 1 ml aliquots of phosphate buffered saline to remove extracellular calcein. Finally, a 1 ml aliquot of phosphate buffered saline was pipetted into each sample plate. Samples were viewed with florescent microscopy to visually confirm the entry of the nonpermanent calcein resulting from corona charge exposure. The percentage of fluorescing cells was visually estimated based upon the total number of cells in the plates. The table shown below indicates the resulting percentages of fluorescing cells in each sample.

| SAMPLE NUMBER | CORONA EXPOSURETIME | % FLOURESCENT |
| --- | --- | --- |
| 1 | 2 minutes | Less than 1% |
| 2 | 4 minutes | 15% |
| 3 | 6 minutes | 20% |
| 4 | 8 minutes | 30% |
| 5 | 10 minutes | 80% |
| 6 | 0 minutes | 0% |

The results from sample 6 indicate that the absence of corona exposure did not result in the entry of calcein into the cells. However, samples 15 indicate that increasing percentages of cells were fluorescent as the corona exposure time increased. The calcein was located within the interior of the cells with no detectable distribution within the cells.

This data set indicates that applying the corona charge can induce a permeabilized state and suggests that it can be the driving force for one or more of the following 1. movement of the calcein molecules in the extracellular space; 2. modification of the outer cell barrier (cell membrane in this case) and increase its permeability; 3. movement of the molecules within the intracellular space; and 4. movement of molecules from the extracellular space to the intracellular space.

Figure 3:
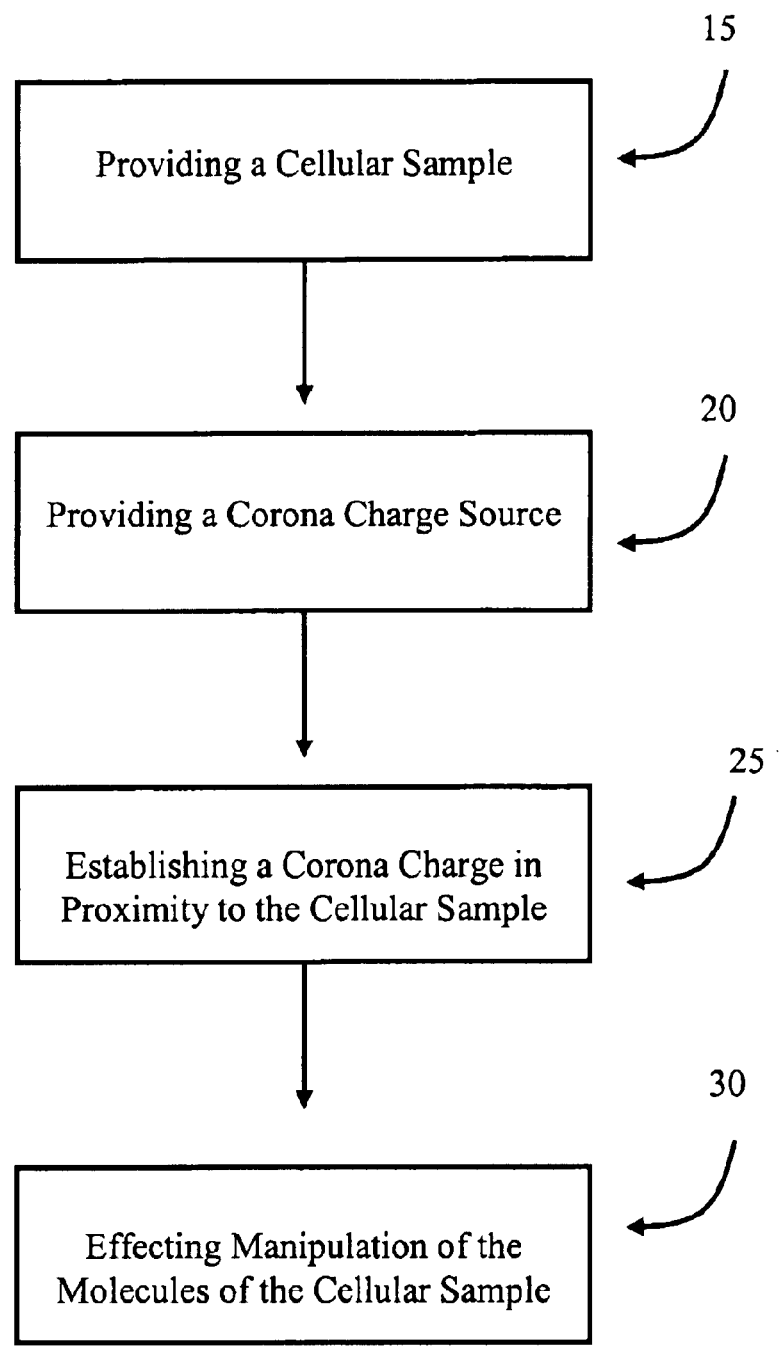
FIG. 3 is a flow diagram of an embodiment of the present invention.

As exemplified by FIG. 3, the present invention can be practiced by a method to include providing a cellular sample 15, providing a corona charge source 20, establishing a corona charge in proximity to the cellular sample 25, and effecting manipulation of the molecules of the cellular sample 30.

Figure 4:
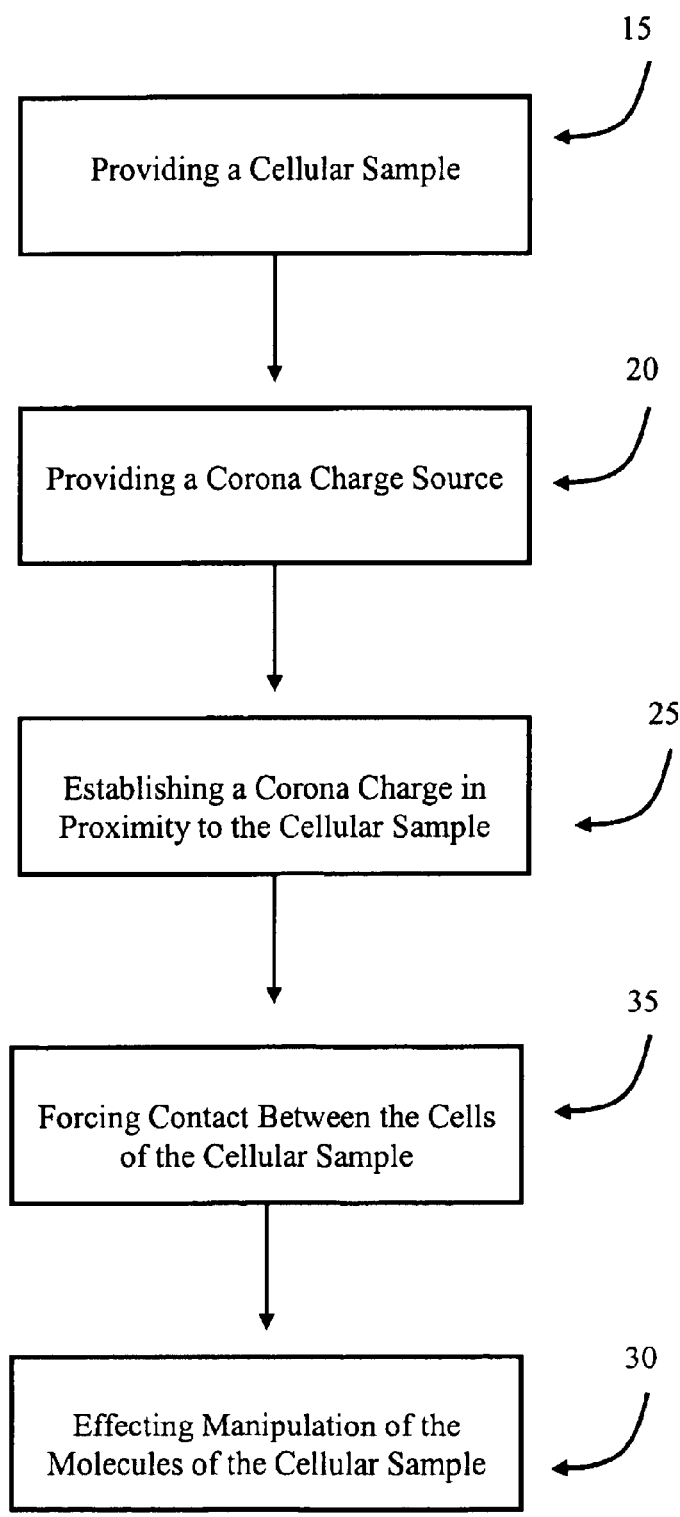
FIG. 4 is a flow diagram of an additional embodiment of the present invention incorporating fusion of cells.

In an additional embodiment, as shown in the flow diagram FIG. 4, in addition to establishing a corona charge in proximity to the cellular sample 25, the cells are forced to contact 35, thereby enabling cell fusion. Procedures that modify the outer barrier of cells can be used to induce the fusion of two or more cells. These include electricity and polyethylene glycol. Fusion partner cells must contact each other in order to fuse. The method of the present invention encompasses variations of this embodied method, to include: exposing the cells of interest to corona charges and subsequently forcing contact between the cells in order to obtain fused cells; forcing cell—cell contact and subsequent modification of the membranes using corona charges to induce fusion; and simultaneously forcing contact and applying corona charge. In all cases, the vessel may or may not have a bias potential applied to it. Some of the methods that can be used to force contact and migration toward one side of a substrate include centrifugation, and dielectrophoresis. The foregoing list is not exhaustive and not intended to be limiting. In addition, the corona charges may be used within tissues to fuse cells that are in close proximity to each other within the tissue structure. Corona emission may also be used to fuse two different tissues together or to fuse cells to tissue.

Figure 5:
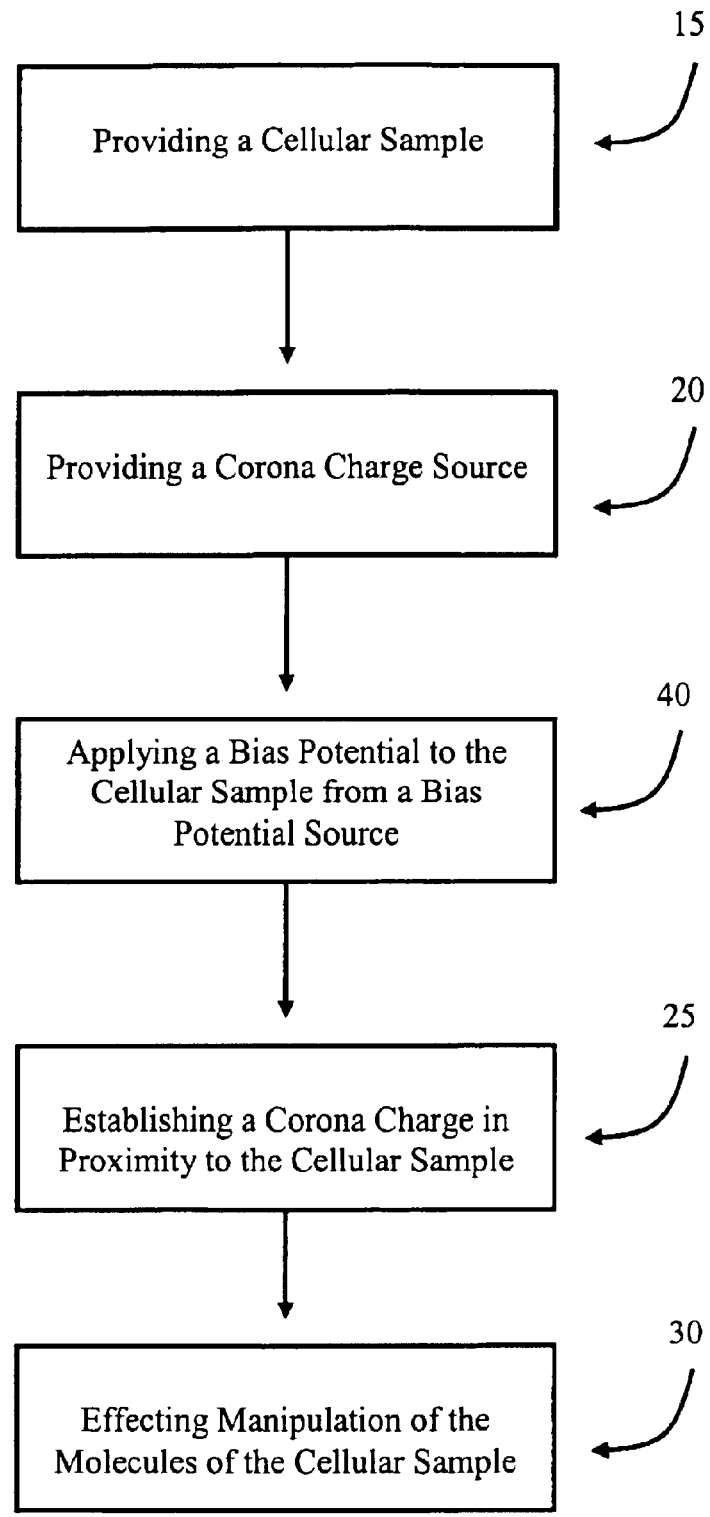
FIG. 5 is a flow diagram of an additional embodiment of the present invention incorporating the establishment of a bias potential.
Figure 6:
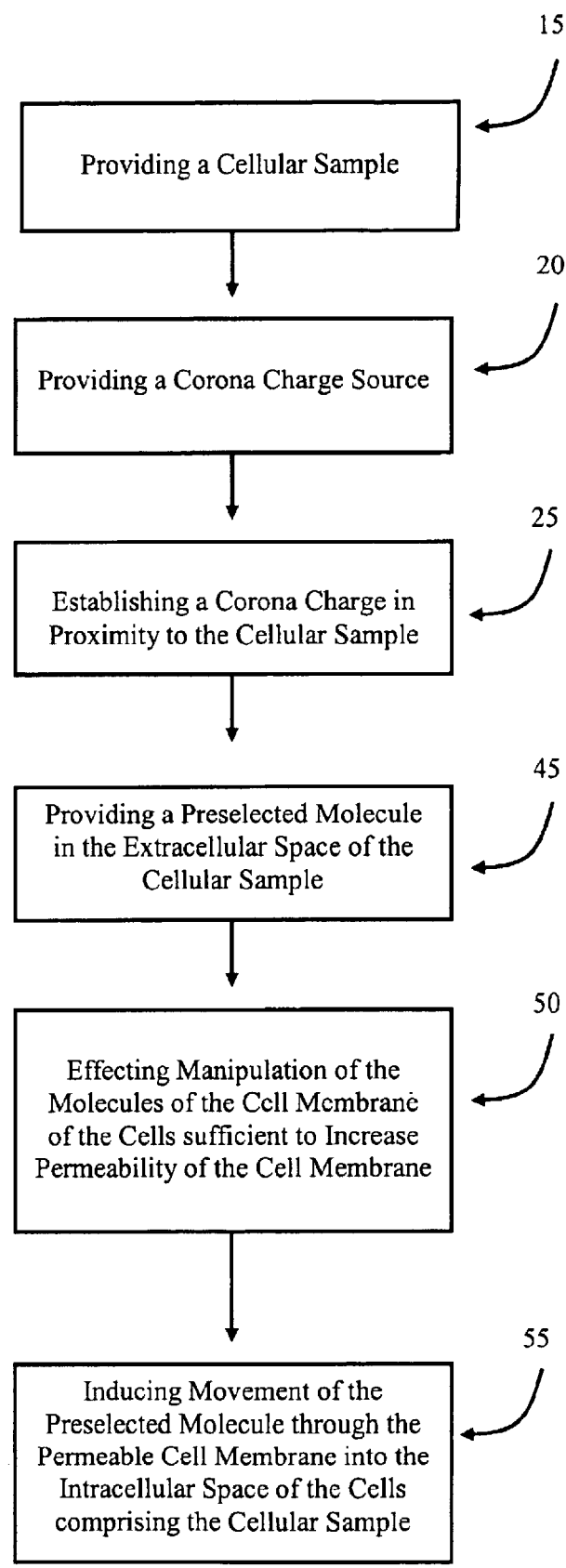
FIG. 6 is a flow diagram of a preferred embodiment of the present invention incorporating the introduction of a preselected molecule.

As shown in FIG. 5, the application of a bias potential 40 to the cellular sample is anticipated by the invention. The application of a bias potential to the cellular sample contributes to the molecular manipulation of the cellular sample. It is within the scope of the present invention to apply a bias potential to induce electroporation of the cells of the cellular sample in cooperation with the application of the corona charge.

In a preferred embodiment of the method of the present invention as illustrated by the flow diagram in FIG. 5, a cellular sample is provided 15, a corona charge source is provided 20, and a corona charge is established in proximity to the cellular sample 25. Additionally, a preselected molecule is provided in the extracellular space of the cellular sample 45. The corona charge effects the manipulation of the molecules of the cell membrane of the cells sufficient to increase the permeability of the cell membrane 50 and further induces the movement of the preselected molecule through the permeable cell membrane 55 and into the intracellular space of the cells comprising the cellular sample.

Figure 7:
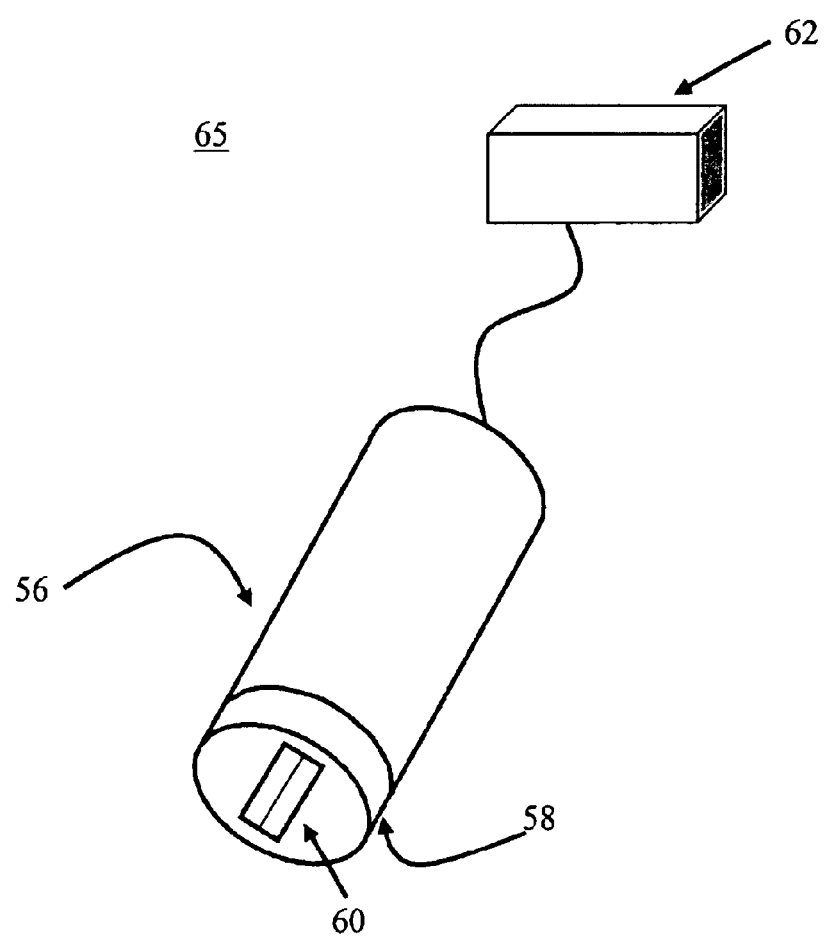
FIG. 7 is a diagrammatic view of a corona charge applicator of the present invention.
Figure 8:
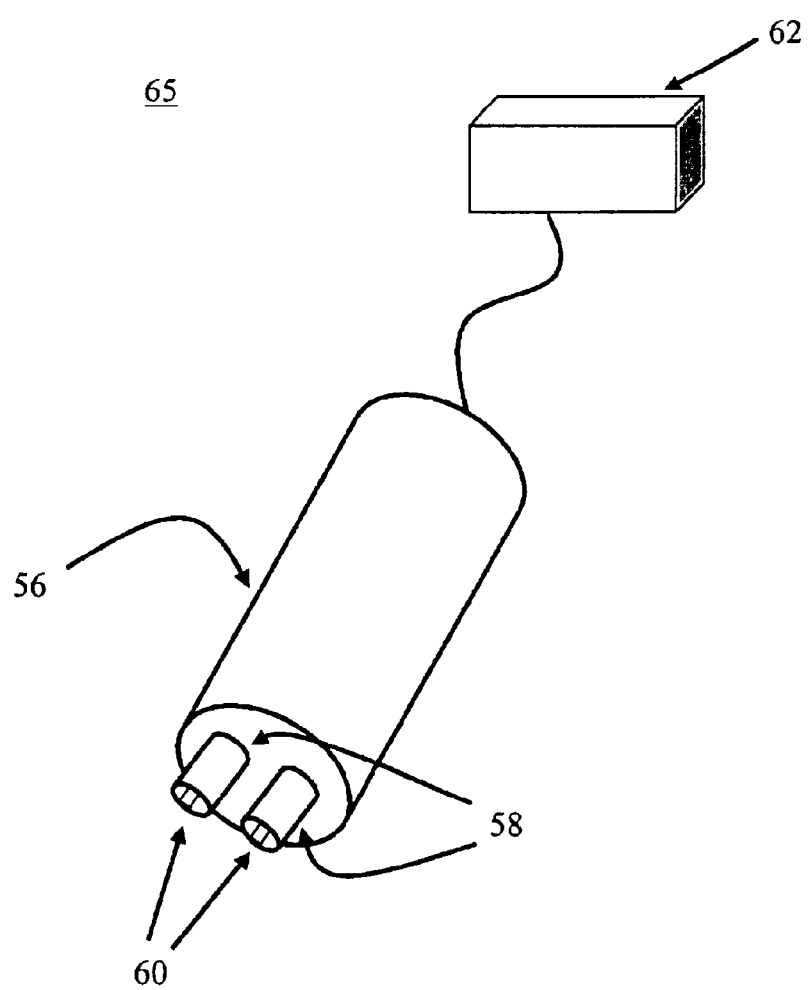
FIG. 8 is a diagrammatic view of the corona charge applicator of the present invention with two corona charge emitters.

FIG. 7 illustrates a preferred embodiment of a corona charge applicator 65 of the present invention adapted to provide a corona charge to cells. The device is comprised of a support 56, at least one support member 58, at least one device for emitting corona ions 60, and a power source 62 in electrical communication with the applicator. As shown in FIG. 8, it is within the scope of the present invention to have a plurality of corona emitting devices 60 existing on a plurality of support members 58. The devices shown in FIGS. 7 and 8 are exemplary. It is considered within the scope of the invention to include devices that have more than one corona emitter on each member, devices with any number of members, members of any physical dimensions, corona emitters of any physical dimensions. In addition, a support member may be an integral part of the support.

Figure 9:
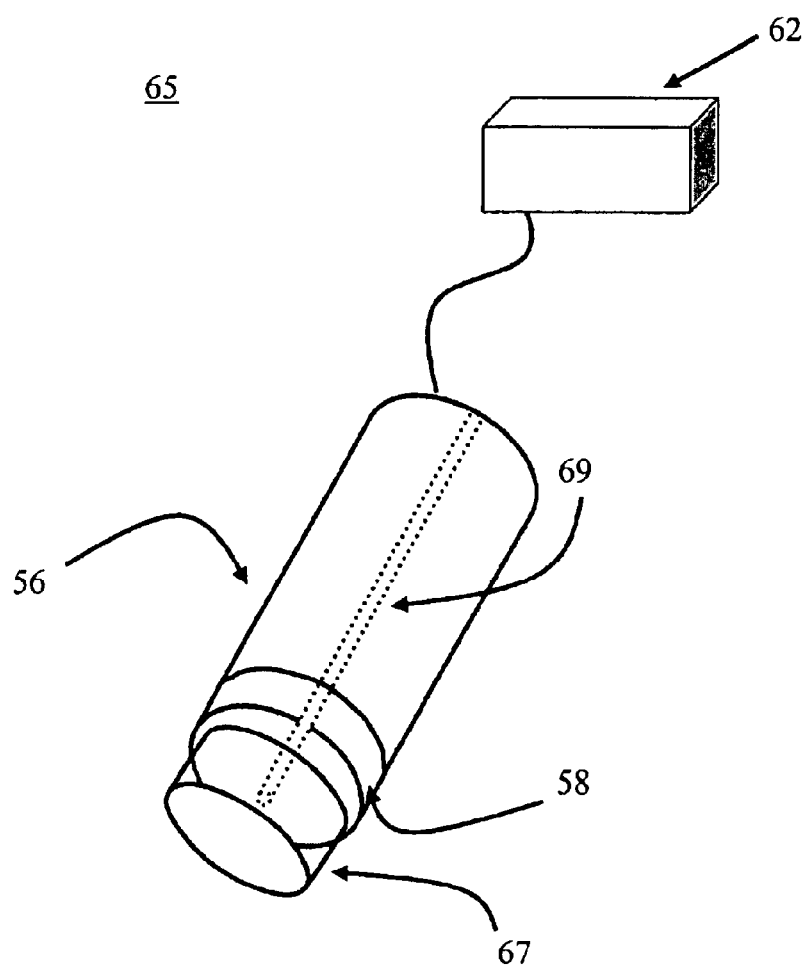
FIG. 9 is a diagrammatic view of the corona charge applicator of the present invention incorporating a spacer.

FIG. 9 illustrated a preferred embodiment of the corona charge applicator 65 further comprising a spacer 67. The spacer 67 is used to define the minimum distance between the corona charge applicator and the target cells that will be treated with the ions. In practical terms the corona charge applicator can be positioned so that the end of the spacer distal to the applicator is in contact with the tissue of interest. Alternatively, the distal end can be located at some measured distance or other physical point for treating cells that are contained in a vessel such as a petri dish. The dimensions of the spacer determine the minimum distance. It is also within the scope of the invention to provide an adjustable spacer adapted to vary the effective dimension of the spacer and thereby adjust the minimum distance between the applicator and the target cells. The spacer 67 as described is adapted to include a portal 69 that allows the introduction of molecules into the cells or area near the cells such as a portal that allows access to the target cells by hypodermic needle or jet injection. This portal may also be used to introduce liquid, gas, vapor, or any other substance.

Figure 10:
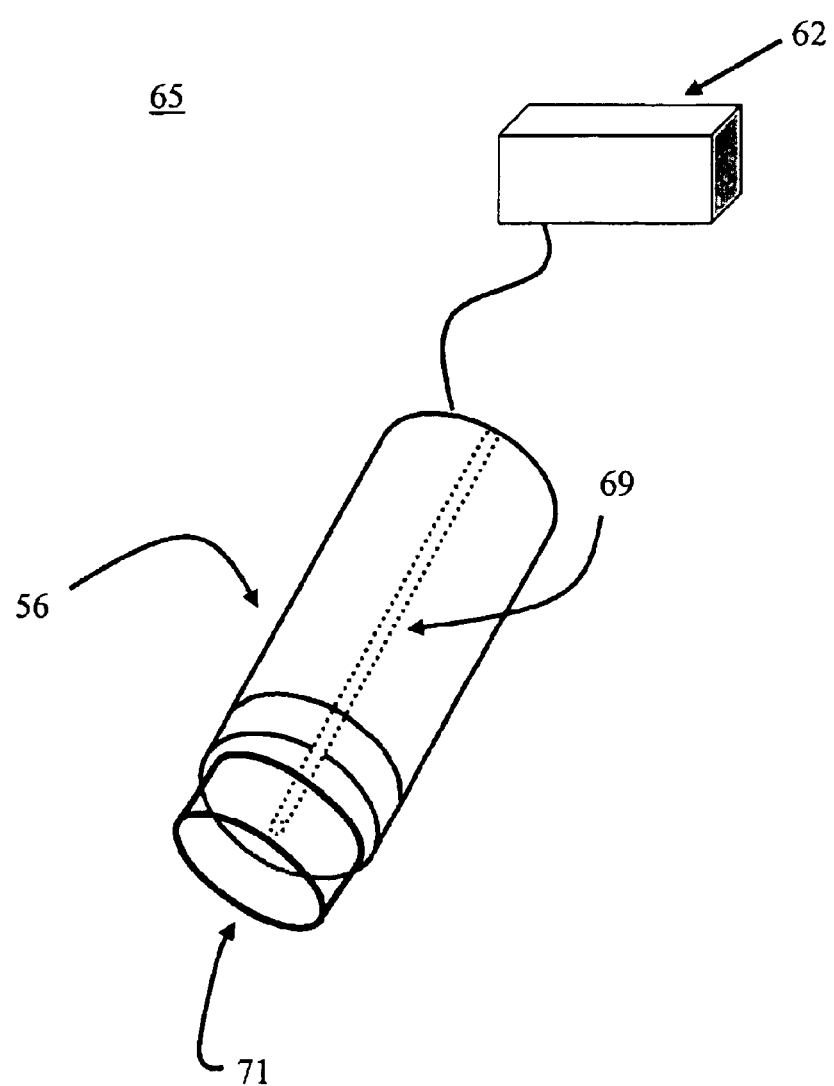
FIG. 10 is a diagrammatic view of the corona charge applicator of the present invention incorporating a restrictor.
Figure 11A:
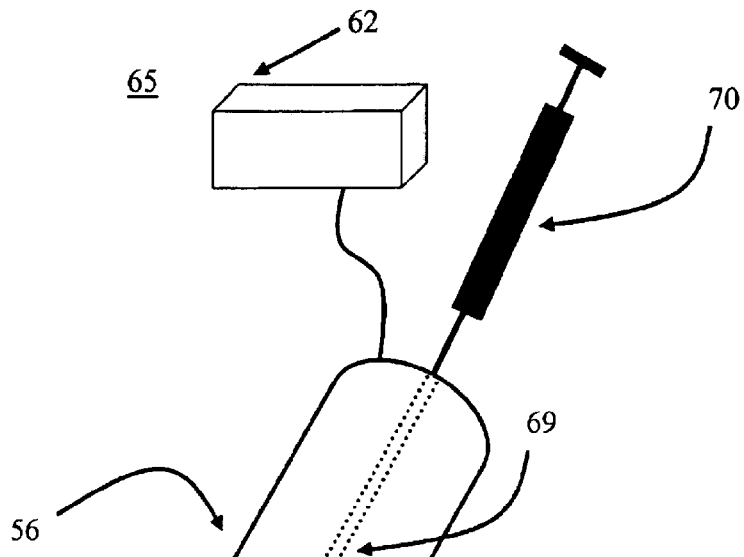
FIG. 11 is a diagrammatic view of the corona charge applicator of the present invention incorporating a portal utilizing a hypodermic needle, FIG. 11a, and a jet injection device, FIG. 11b.
Figure 11B:
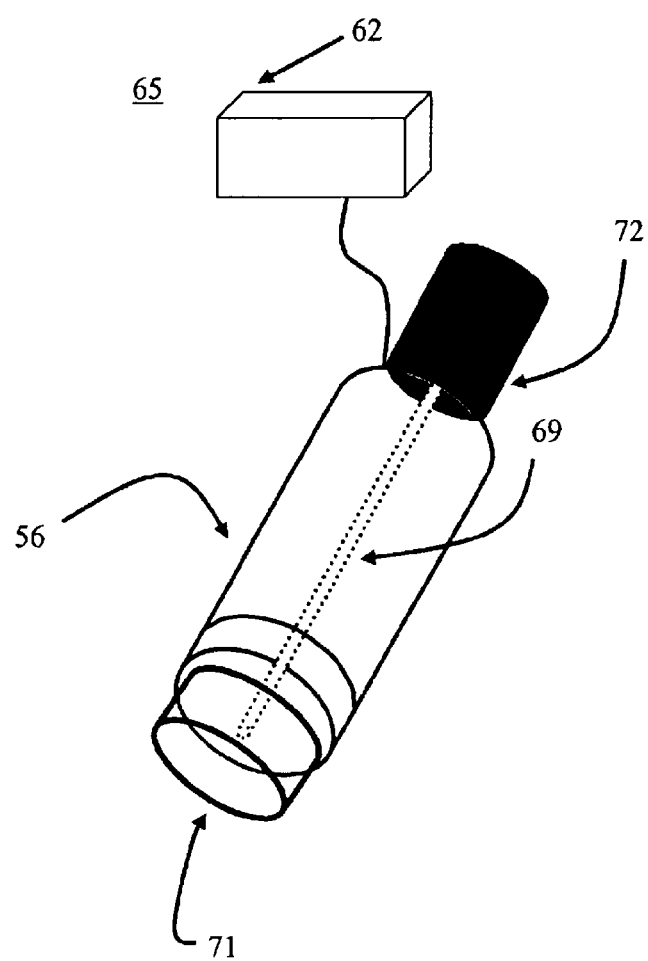

In an additional embodiment of the corona charge applicator 65, as shown in FIG. 10, the area of charge flux can be controlled by a restrictor located near the corona emission end of the corona charge applicator. In the exemplary embodiment of FIG. 10, the restrictor is shown as a hollow cylinder 71. The area of charge flux is restricted to the area of the hollow core of the cylinder. Thus, the device shown in the figure would limit ion flux to a circular area. It is within the scope of the present invention to provide a restrictor exhibiting a variety of shapes as necessary for the application of the corona charge, to include shapes to fit a specific tissue segment under treatment, such as the eye, the shape of a tumor, or the shape of a tissue culture vessel. A variety of shapes are anticipated, to include circular, elliptical, rectangular, pentagon, triangular, and freeform. Additionally, the restrictor and spacer may be integral to each other. It is within the scope of the invention for the restrictor and support to accommodate a portal 69 that allows the introduction of molecules into the cells or area near the cells such as a portal that allows access to the target cells by hypodermic needle or jet injection. This portal may also be used to introduce liquid, gas, vapor, or a variety of other substances. FIG. 11a illustrates the use a hypodermic needle 70 passed through the portal to introduce a molecule of interest to a location that in near the target cells as described. FIG. 11b illustrates the use of a jet injection device 72 to perform the same function. It is within the scope of the invention to provide a means for introducing the molecule of interest into the target tissue as an integrated part of the corona applicator or independent of the applicator.

Figure 12:
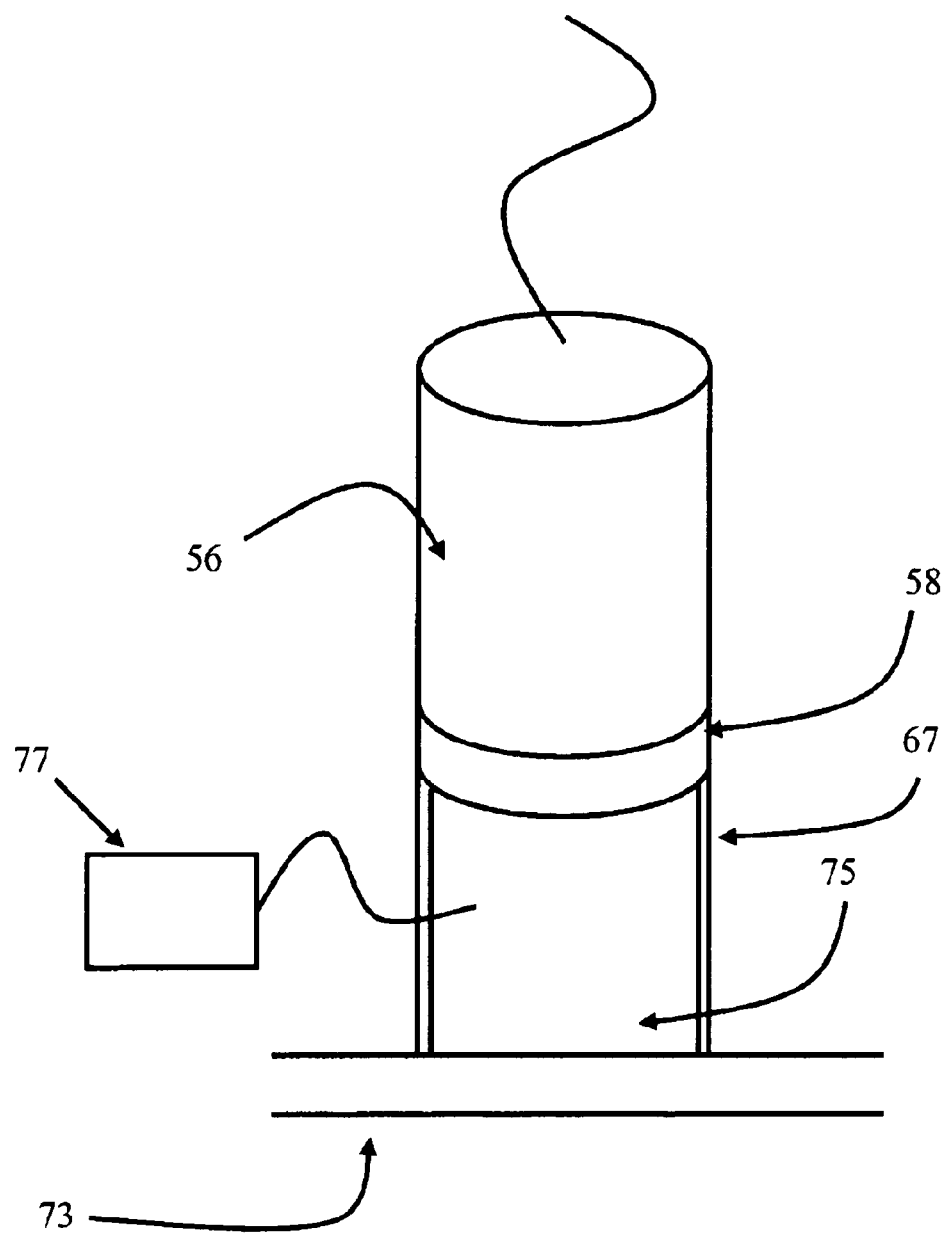
FIG. 12 is a diagrammatic view of the corona charge applicator of the present invention incorporating an airtight cavity.

As shown in FIG. 12, the spacers and restrictors as previously described are adapted to allow control of the environment between the target cells 73 and the corona charge applicator. It is known that the type of charge and number of charges produced utilizing a corona charge is dependent upon the humidity and gaseous composition of the environment near the corona emitter. The restrictor and spacer of the present invention are adapted to isolate the space between the corona emitter 58 and target cells 73. This can be achieved when treating tissue, for example, pressing the distal end of the spacer 67 or against the tissue 73 thereby causing a substantially effective seal resulting between the spacer and the tissue creating a substantially air tight cavity 75, limiting the exchange of gases between the external environment and the environment between the corona emitter and the target tissue. The composition of the environment within this airtight cavity can then be controlled and adjusted with an atmospheric controller 77. The atmospheric controller 77 is envisioned to be a syringe, pump, fan or other technology known in the art. Controlling the environment within the airtight cavity may include changing the or composition of other gasses.

Figure 13:
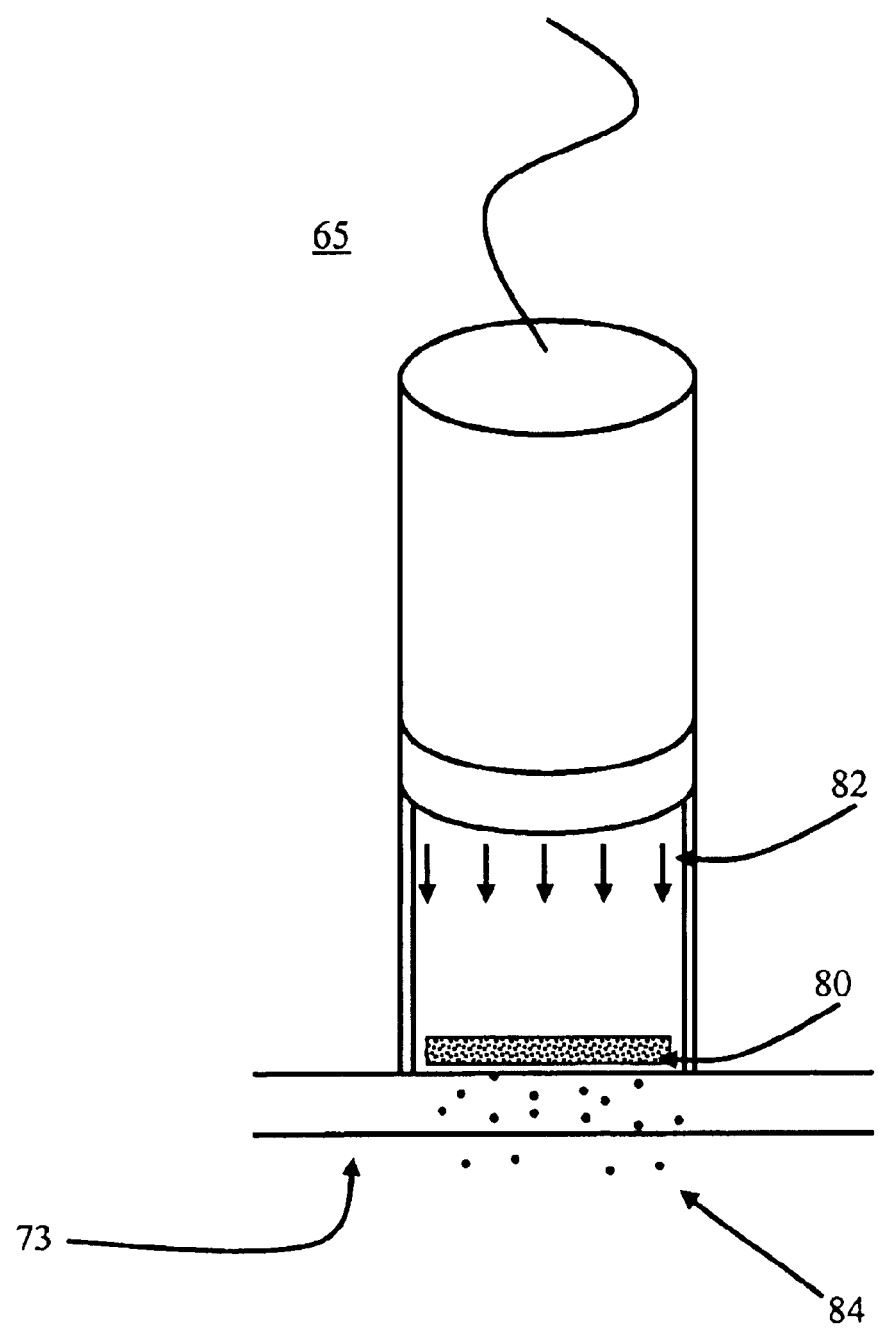
FIG. 13 is a diagrammatic view of the corona charge applicator of the present invention incorporating a reservoir.
Figure 14:
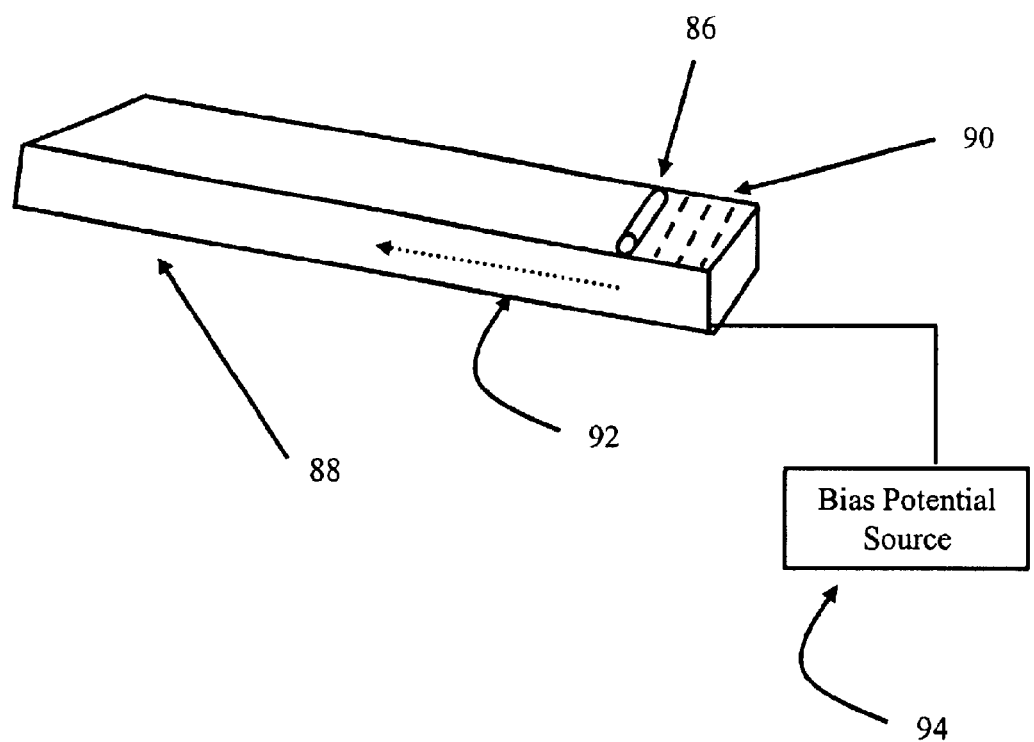
FIG. 14 is a diagrammatic view of the corona charge applicator of the present invention incorporating a holding apparatus allowing for gel electrophoresis.
Figure 15:
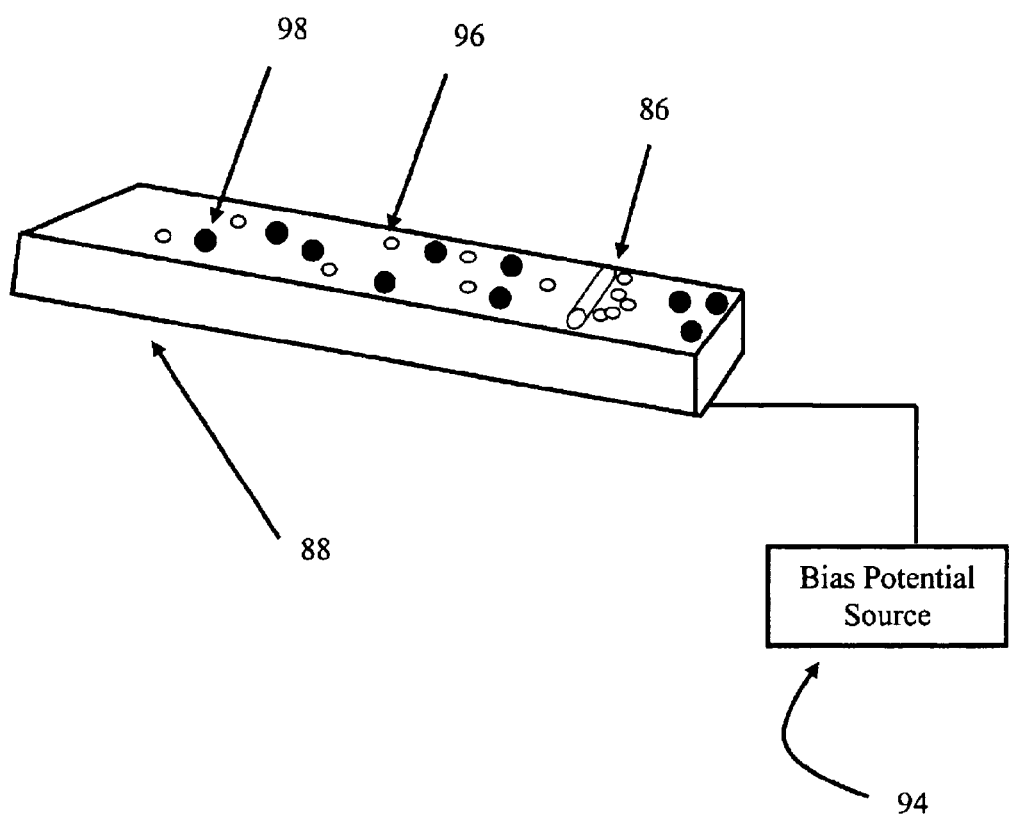
FIG. 15 is a diagrammatic view of the corona charge applicator of the present invention incorporating a holding apparatus allowing for gel electrophoresis.

As exemplified by FIG. 13, a reservoir 80 adapted to hold molecules that are to be manipulated using the corona charge applicator. Is it envisioned that the reservoir contains one or more different molecule types of interest. Additionally, the reservoir may be comprised of a solid structure, a liquid, gel, emulsion, absorbent substance, or porous substance. In a preferred embodiment, the reservoir is a patch of absorbent material soaked with a solution of the molecule of interest. This patch may be located on the distal end of the spacer or restrictor. This arrangement would allow a supply of the molecule of interest to be near the target cells for manipulation relative to the physical position of the cells. In an additional embodiment, the reservoir is a cream containing the molecule of interest applied to the tissue. A layer of cream placed on the surface of the tissue prior to the application of corona charges will serve to manipulate the molecule of interest relative to the cells of the tissue. As in FIG. 13, the corona charge applicator 65 is positioned at a distance away from the tissue 73. Ions are emitted 82 to a reservoir 80 that is on or near the surface of the skin. The corona ions repel the molecule of interest that is located in the reservoir. This repulsion leads to the migration of the molecules of interest in a direction that is away from the corona ions at the surface of the skin 84. It is envisioned that corona ions can be used to move molecules through any tissue or fraction of a tissue using the principles illustrated in FIG. 13.

It is within the scope of the present invention to utilize corona charge to manipulate molecules in a nonliving matrix such as done by traditional gel electrophoresis. As shown in FIG. 14, a holding apparatus 88 is provided to contain a cellular sample, such as a nonliving matrix. A corona charge emitter 86 is adapted to move over the gel in the direction 92, the gel being loaded with molecules to be moved. Movement of the corona charge may be through mechanical or physical means. As the corona emitter moves along the direction shown 92, the molecules 90 separate within the gel. Alternatively, the corona emitter may be stationary and the gel may be movable. Additionally, a bias source 94 may be provided for the application of a bias potential to the nonliving matrix or gel.

Additionally, the method and apparatus of the present invention are adaptable and can be exploited to cause a separation of cells with dissimilar charge. As shown in FIG. 18, the application of a charge utilizing the corona charge applicator 86 to the surface of a medium bathing the cells. In this example two types of cells, 96 and 98, exhibiting differing charge properties are contained within a holding apparatus 88. The movement of the corona charge applicator 86 along the surface of the medium will result in a fraction of the cells to be attracted to the charge, in this case 96, in a manner that is stronger than other cells. The end result will be that the region of liquid that is receiving corona charge will be enriched with cells that have particular properties. Therefore, this embodiment is effective for the separation of cells exhibiting differing charge properties.

For the purposes of this invention corona charge is defined as ionic charge produced by an electrical conductor that is not in contact with the target cells. Corona charge can be either +, or alternating (AC) for the devices and methods described above and in the claims. In addition, both species of ions can be generated simultaneously by any of the devices and for any of the methods described in this document. The corona charge may be applied constantly or in a manner that is not constant such as but not limited to pulsed exposure to corona charges. The magnitude and duration of the treatment with corona charge is dependent upon the particular combination of molecule(s) and cells(s) under investigation as well as the intended purpose of the applied charges It may be appreciated by one of skill in the art that biological cells exist in many forms and in many types. The devices and methods described in this document apply to all types of living cells including prokaryotes, eukaryotes, plant cells. Therefore, the term cell is to be broadly interpreted. In addition, the term cell also includes artificial cells such as liposomes and micelles for the purposes of this document as the methods and devices described can be applied to these entities also. The term cell in the description above and in the claims also has additional meaning which encompasses a single cell, cells in culture, cell aggregates, and a cell that is part of a tissue.

The term molecule has been used throughout this document and is to be defined as any type of molecular species. The devices and methods described herein are particularly applicable to therapeutic drugs, proteins, nucleic acid sequences, and plasmid DNA but can by applied to any type of molecule. In addition, the devices and methods are applicable for simultaneously affecting more than 1 type of molecule. And furthermore, the manipulation of these molecules and cells can be for the purposes of the enhancement of therapeutic molecules for the treatment of disease or for the prevention (such as vaccine) of disease. The devices and methods described herein can be applied to any tissue type either in vivo or in vitro. In addition to the use of this for combating disease, the instant invention can be used for research purposes. The devices and methods described herein can be used for diagnostic and/or molecular identification purposes.

It will thus be seen that the objects set forth above, and those made apparent form the foregoing description, are efficiently attained. Since certain changes may be made in the foregoing construction without departing from the scope of the invention, it is intended that all matters contained in the foregoing construction or shown in the accompanying drawing shall be interpreted as illustrative and not in a limiting sense. It is also to be understood that the following claims are intended to cover all of the generic and specific features of the invention herein described, and all statements of the scope of the invention which, as a matter of language, might be said to fall there between.

The invention claimed is

What is claimed is:

1. A method to facilitate the manipulation of molecules of a biological cellular sample, the method comprising the steps of:

providing a biological cellular sample;

providing a corona charge source;

positioning the corona charge source proximate to the cellular sample; and establishing a corona charge in proximity to the cellular sample whereby the establishment of the corona charge is effective in manipulating the molecules of the cellular sample.

2. The method of claim 1, further comprising the step of applying a bias potential to the cellular sample.

3. The method of claim 1, further comprising the step of introducing a preselected molecule into the extracellular space of the cellular sample.

4. The method of claim 3, further comprising the step of manipulating the preselected molecule within the extracellular space.

5. The method of claim 3, further comprising the step of inducing movement of the preselected molecule in the extracellular space such that the molecule passes through the permeable cell membrane into the interior of the cell.

6. The method of claim 1, further comprising the step of inducing movement of an intracellular molecule into the extracellular space of the cellular sample.

7. The method of claim 1, further comprising the step of moving the corona charge source in a predetermined direction relative to the cellular sample.

8. The method of claim 1, further comprising the step of moving the cellular sample in a predetermined direction relative to the corona charge source.

9. A method of fusing two or more biological cells, comprising the steps of:
   providing a biological cellular sample;
   providing a corona charge source;
   forcing contact between two or more cells of the cellular sample; and
   positioning the corona charge source proximate to the cellular sample, whereby fusion of the two or more cells is effected.

10. The method of claim 9, further comprising the step of applying a bias potential to the cellular sample.

11. A method to facilitate the entry of a preselected molecule into the intracellular space of a biological cellular sample, the method comprising the steps of:
   providing a biological cellular sample, the sample comprising cells and extracellular space;
   providing a corona charge source;
   establishing a corona charge in proximity to the cellular sample to increase the permeability of the cell membrane; and
   inducing movement of a preselected molecule in the extracellular space such that the molecule passes through the permeable cell membrane into the intracellular space of a cell of the cellular sample.

12. The method of claim 11, further comprising the step of applying a bias potential to the cellular sample.

13. The method of claim 11 further comprising the step of introducing the preselected molecule into the extracellular space of the cellular sample.

14. An apparatus to facilitate the manipulation of molecules of a biological cellular sample, the apparatus comprising:
   a support member; and
   at least one biological molecule manipulating corona charge emitting device extending away from the support member, the biological molecule manipulating corona charge emitting device generating a corona charge in proximity to the cellular sample for the effective manipulation of the molecules of the biological cellular sample.

15. The apparatus of claim 14 wherein the corona charge emitting device is affixed to the support member.

16. The apparatus of claim 14 wherein the corona charge emitting device defines the support member.

17. The apparatus of claim 14 further comprising a spacer circumferentially encompassing the corona charge emitting device, the spacer defining the proximity of the corona charge emitting device relative to the cellular sample.

18. The apparatus of claim 17 wherein the spacer is substantially transparent.

19. The apparatus of claim 14 further comprising a restrictor circumferentially encompassing the corona charge emitting device, the restrictor defining a restricted area of the cellular sample in which the corona charge is generated.

20. The apparatus of claim 19 wherein the restricted area is a predetermined geometric configuration.

21. The apparatus of claim 19, wherein the restrictor is substantially transparent.

22. The apparatus of claim 19, whereby contact between the restrictor and the cellular sample establishes a substantially airtight cavity.

23. The apparatus of claim 22, further comprising an atmospheric controller in communication with the airtight cavity, the atmospheric controller adapted to regulate the air within the cavity.

24. The apparatus of claim 14, further comprising a portal surrounded by the support member, the portal positioned to accommodate a device adapted for the introduction of a molecule of interest into the cellular sample.

25. The apparatus of claim 24, wherein the device adapted for the introduction of a molecule of interest is selected from the group consisting of, a hypodermic needle, or a jet injection apparatus.

26. The apparatus of claim 14, further comprising a reservoir positioned between the corona charge emitter and the cellular sample, the reservoir containing a molecule of interest.

27. The apparatus of claim 14, further comprising a cellular sample holding apparatus to contain the cellular sample.

28. The apparatus of claim 27, further comprising means for moving the corona charge emitting device in a predetermined direction relative to the cellular sample.

29. The apparatus of claim 27, further comprising means for moving the cellular sample in a predetermined direction relative to the corona charge emitting device.

* * * * *

UNITED STATES PATENT AND TRADEMARK OFFICE
CERTIFICATE OF CORRECTION

PATENT NO.     : 6,929,949 B1
DATED          : August 16, 2005
INVENTOR(S)    : Drew Hoff et al.

It is certified that error appears in the above-identified patent and that said Letters Patent is hereby corrected as shown below:

Title page,
Item [75], Inventors, "Drew Hoff" should be changed to -- Andrew M. Hoff --.

Signed and Sealed this

Eighth Day of November, 2005

JON W. DUDAS
*Director of the United States Patent and Trademark Office*